US011602388B2

(12) United States Patent
Holsing et al.

(10) Patent No.: US 11,602,388 B2
(45) Date of Patent: Mar. 14, 2023

(54) ABLATION MONITORING SYSTEM AND METHOD

(71) Applicant: Veran Medical Technologies, Inc., St. Louis, MO (US)

(72) Inventors: Troy L. Holsing, Golden, CO (US); Mark Hunter, St. Louis, MO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 813 days.

(21) Appl. No.: 16/546,652

(22) Filed: Aug. 21, 2019

(65) Prior Publication Data

US 2021/0052314 A1 Feb. 25, 2021

(51) Int. Cl.
*A61B 18/02* (2006.01)
*A61B 18/14* (2006.01)
*A61B 8/12* (2006.01)
*A61B 90/00* (2016.01)
*A61B 18/00* (2006.01)

(52) U.S. Cl.
CPC ............ *A61B 18/02* (2013.01); *A61B 8/12* (2013.01); *A61B 18/1492* (2013.01); *A61B 90/37* (2016.02); *A61B 2018/00583* (2013.01); *A61B 2018/00702* (2013.01); *A61B 2018/00791* (2013.01); *A61B 2018/0212* (2013.01); *A61B 2090/378* (2016.02)

(58) Field of Classification Search
None
See application file for complete search history.

(56) References Cited

U.S. PATENT DOCUMENTS

| 5,741,248 | A  | 4/1998 | Stern et al. |
| 6,905,492 | B2 | 6/2005 | Zvuloni et al. |
| 7,402,161 | B2 | 7/2008 | Zvuloni et al. |
| 7,937,132 | B2 | 5/2011 | Piron et al. |
| 8,685,014 | B2 | 4/2014 | Babkin et al. |

(Continued)

FOREIGN PATENT DOCUMENTS

WO WO-2017167762 A1 * 10/2017 ........... A61B 5/0035

OTHER PUBLICATIONS

Image-guided Interventions, second ed. Matthew A Mauro et al., Expert radiology series ebook, published by Sauders/Elsevier, Philadelphia, PA. USA 2014.

(Continued)

*Primary Examiner* — Ronald Hupczey, Jr.
(74) *Attorney, Agent, or Firm* — Forsgren Fisher; Daniel A. Tysver; James M. Urzedowski

(57) ABSTRACT

A system and method are presented for treating targeted tissue using cryoablation. An introducer canula and a cryoprobe are inserted the targeted tissue. The cryoprobe is cooled and an ice ball is formed. The cryoprobe is removed while the ice ball is still frozen, and an ultrasound catheter is inserted. Ultrasound generated within the ice ball is used to determine the distance from the ultrasound catheter to a perimeter of the ice ball. This is repeated at different angles to model a slice of the ice ball. The ultrasound catheter is moved radially, and the process is repeated to create a model of at least a portion of the ice ball. The ice ball model can be displayed on a registered set of images representing the targeted tissue to ensure that the tissue lies within the treatment zone of the ice ball.

20 Claims, 8 Drawing Sheets

(56) References Cited

U.S. PATENT DOCUMENTS

| | | | |
|---|---|---|---|
| 8,695,549 | B2 | 4/2014 | Richter |
| 9,820,798 | B2 | 11/2017 | Schwartz |
| 9,918,792 | B1 | 3/2018 | Boveja et al. |
| 10,413,185 | B1 | 9/2019 | Boveja et al. |
| 2007/0185554 | A1* | 8/2007 | Appling ............. A61B 18/1815 607/101 |
| 2015/0087975 | A1* | 3/2015 | Salcudean ............. A61B 8/485 606/20 |

OTHER PUBLICATIONS

Temperature Monitoring During Tissue Freezing Using Ultrasound Speed Measurements, by I. Jovanovic et al. vol. 7265, Proc. SPIE 7265, Medical Imaging 2009: Utrasonic Imaging and Signal Processing, edited by Stephen A. McAleavey and Jan D'hooge. 2009.
In Vivo Results with a New Device for Ultrasonic Monitoring of Pig Skin Cryosurgery: The Echographic Cryoprobe by Pascal Laugier et al. Laboratoire d'Imagerie Parame'trique, URA CNRS, Paris, France; 1998 La Motte d'Aveillans, France; Laboratoire de Radiobiologie Applique'e, CEA, Gif-sur-Yvette, France. vol. III, No. 2 Skin Echo-Cryosurgery. The Society for Investigative Dermatology, Inc. 1998.
Cancer Cryotherapy: Evolution and Biology, by Dan Theodorescu, MD, PhD. Reviews in Urology 2004; 6(Supp4):S9-S19 MedReviews LLC 2004.

\* cited by examiner

ABLATION MONITORING SYSTEM AND METHOD

FIELD OF THE INVENTION

A medical device ultrasound catheter system and method is presented to allow for ice ball size, shape, and positioning determination in cryosurgery. A similar system and method is usable to measure the size, shape, and positioning of heat-ablated tissue.

BACKGROUND OF THE INVENTION

Cryosurgery or cryoablation is a procedure in which abnormal or target tissue is destroyed through a freezing process. The freezing of tissue cells causes the cells or organelles within the cells to rupture. The cryosurgery process requires the insertion of a device (a "cryoprobe") into the abnormal tissue and then cooling the device. In most circumstances, the cooling of the cryoprobe is accomplished by passing a high-pressure gas, such as argon, through the device. The cooling of the cryoprobe in this manner creates an "ice ball" of frozen tissue that is approximately centered on the distal end of the cryoprobe.

It is important that the size, shape, and location of the ice ball be accurately determined in order for the procedure to be successful. If the ice ball is larger than necessary, healthy tissue surrounding the target tissue will be unnecessarily damaged. If the ice ball is too small, abnormal tissue that was to be killed through the process will survive.

Traditionally, the size and positioning of the ice ball is determined through ultrasound technology. The ultrasound energy passes through normal tissue and then hits the external surface of the ice ball. Because of the characteristics of the ice ball, ultrasound energy will typically bounce off the ice ball. This large reflection allows ultrasound imaging techniques to image the surface of the ice ball closest to the source of ultrasound energy. Unfortunately, the ultrasound energy is unable to penetrate the ice ball and is unable to show the true three-dimensional size and shape of the ice ball due to the "shadow" cast by this surface reflection. In essence, the existing methodology allow the user to find the approximate location of the nearest surface of the ice ball but not its true size, shape, or location.

SUMMARY

One embodiment of the present invention presents a method for treating a tumor or other targeted tissue using cryoablation. The method begins by identifying the location of the targeted tissue, such as by performing pre-procedure CT imaging. The images created can be combined into 3-D images, or into a 3-D model of the patient or of an organ of the patient. During the procedure, an ultrasound catheter contained within an inducer canula is inserted into the targeted tissue. In one embodiment, the ultrasound catheter and canula are inserted percutaneously. Once positioned, the ultrasound catheter can be used to image the targeted tissue and to ensure proper positioning of the catheter and canula. The ultrasound catheter may be capable of QUS analysis of the tissue.

Once the position of the ultrasound catheter and canula are confirmed, the ultrasound catheter is removed from the canula and a cryoprobe is inserted into its place. Alternatively, the cryoprobe and canula could be directly inserted percutaneously into the targeted tissue without the use of the ultrasound catheter. In this alternative embodiment, the cryoprobe is positioned through the aid of external ultrasound to ensure the tip of the cryoprobe is correctly positioned within the targeted tissue. In some circumstances, it is necessary to insert multiple cryoprobes into the targeted tissue in order to provide some control over the size and shape of the ice ball created by the cryoablation process.

The cryoprobes are then cooled in order to create an ice ball within the patient. Ideally, the ice ball will be large enough to entirely encompass the targeted tissue. To increase the effectiveness of the ice ball in killing the targeted tissue, the ice ball will frequently be generated, allowed to thaw, and then regenerated by cooling the cryoprobes a second time.

The cryoprobe in the introducer canula is then removed while the ice ball is still frozen. An ultrasound catheter is inserted into the canula and into the channel in the ice ball left by the removal of the cryoprobe. Using a pulse-echo technique and beamforming, a strong signal is emitted from the ultrasound transducer(s) at the end of the ultrasound catheter in a single, radial direction. The same direction is then monitored for ultrasound energy reflected from the outer periphery of the ice ball. Using the time taken for the return of the ultrasound signal, and the known speed of ultrasound in frozen tissue, the radial distance from the ultrasound transducers to the edge of the ice ball in the selected direction is known. A similar signal is transmitted and received in other directions so as to generate information sufficient to model a slice having the same shape and size as the portion of the ice ball just examined by the ultrasound beams. The ultrasound catheter can then be moved slightly within the canula a known distance, and the process is repeated to create a second slice. When this process has been repeated enough time to calculate slices for the entire ice ball, the slices are combined into a single model showing the size and shape of the ice ball.

In one embodiment, the ultrasound catheter contains EM sensors at its tip. Using a system of EM navigation, the position and orientation of the ultrasound catheter can be determined for each created slice of the ice ball model. Assuming that the EM navigation system is registered to the pre-procedure CT images or model, the created model of the ice ball can be superimposed on the CT images. Because the CT images identify the size and location of the targeted tissue, it will be apparent whether the generated ice ball completely incorporated the targeted tissue within its effective treatment area. In some embodiments, software compares the known size, shape, and location of the targeted tissue against the determined size, shape, and location of the generated ice ball and provides a warning if the targeted area was not within the treatment zone of the ice ball. If necessary, a new ice ball can be created to treat the missed portion of the targeted area, and another model of this new ice ball can be generated to ensure the effectiveness of the treatment.

Cryoablation is only one ablation technique for which embodiments can be used to determine the size, shape, and position of ablated tissue. A similar system and method can be used with heat-ablation, such as microwave or radio-frequency ablation. The ultrasound catheter is inserted into heat-ablated tissue, and the pulse-echo technique can be used to create model slices of the ablated tissue. Multiple slices can then be combined into a complete model of the ablated tissue, which can be shown on a 3-D image of the targeted tissue to determine the effectiveness of the ablation.

DETAILED DESCRIPTION

Ice Ball Formation

Figure 1:
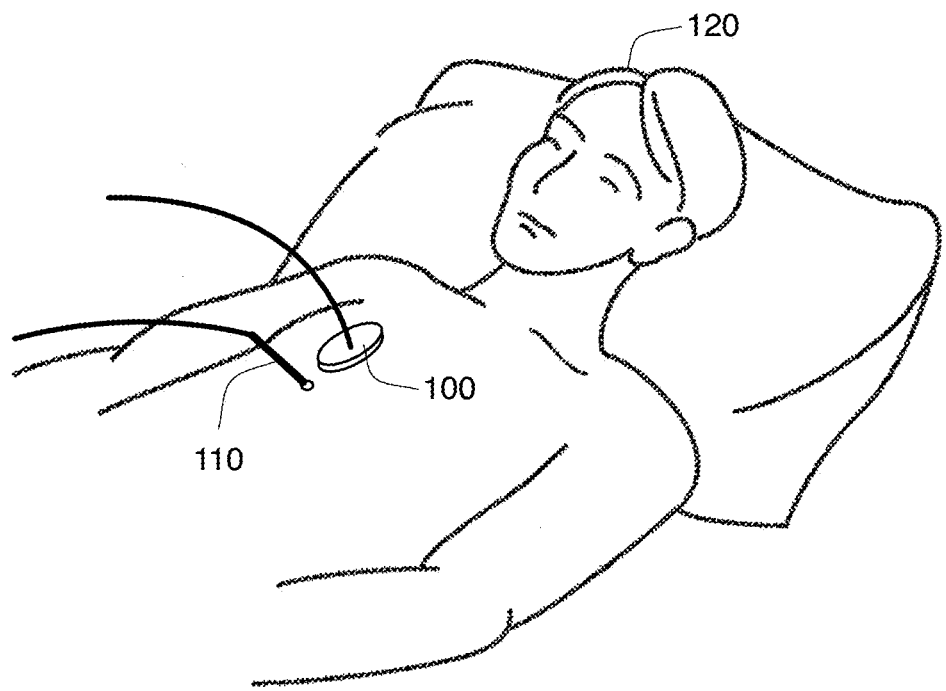
FIG. 1 is a side perspective view of the percutaneous insertion of a cryoprobe under the guidance of ultrasound.

Cryoablation is typically performed to kill abnormal tissue that has been discovered in a patient prior to the procedure. In most cases, the exact location of the abnormal tissue is identified through imaging using traditional technologies such as CT or MRI imaging. After determining that cryoablation is appropriate for the abnormal tissue, the patient is prepared and the abnormal tissue is re-located before beginning the procedure. In FIG. 1, an external ultrasound device 100 is used to identify the location of the targeted tissue. This same ultrasound device is then used to monitor the insertion of the tip of a cryoprobe 110 into a patient 120. The tip of the cryoprobe 110 may be specially designed to improve identifiability of the tip under ultrasound, such as by applying grooves or other physical aberrations which are highly visible to the ultrasound energy. In this manner, the tip of the cryoprobe 110 is percutaneously directed to the target tissue. As explained below in connection with FIG. 14, it is also possible to identify the location of the target tissue and position the cryoprobe 110 using an inserted ultrasound catheter.

Not shown in FIG. 1 are the computer systems that determine which signals and how much power to send to the ultrasound device 100 and cryoprobe 110, send the signals and power to those devices 100, 110, receive signals from those devices 100, 110, analyze those signals, and then display the results of that analysis to the user. Computer systems that control and analyze the signals and power sent to and from the devices used in the disclosed embodiments are standard computer systems that comprise CPUs, short- and long-term memory storage, computer programming, display systems, and interfaces to communicate with devices such as devices 100, 110. Computer systems such as these also control the signals sent to and from the devices described below, and are responsible for performing the calculation and presentation steps in the methods set forth below, including method 1400 of FIG. 14.

Figure 2:
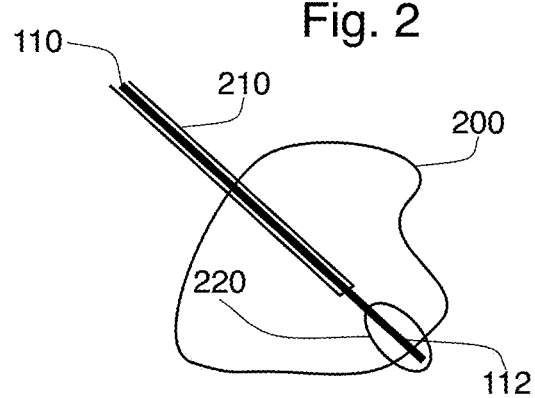
FIG. 2 is a schematic illustration of the cryoprobe of FIG. 1 penetrating the targeted tissue and generating an ice ball.

FIG. 2 shows the distal end or tip 112 of the cryoprobe 110 after it has been inserted into the abnormal target tissue 200 of the patient 120. In FIG. 2, the cryoprobe 110 passes through the lumen of an introducer canula 210 that has been positioned at the target tissue 200. While an introducer canula 210 is not always needed in cryoablation procedures, the ability to locate additional catheter devices at the target tissue 200 makes its use beneficial to most embodiments of the present invention.

Once the tip 112 of the cryoprobe 110 is inserted into the target tissue 200, argon gas is passed through the probe 110. The design of the probe 110 causes the gas to expand at or near the tip 112. Since argon gas cools upon expansion, this expansion causes very rapid cooling of the tip 112 of the probe 110. In traditional cryoprobes 110, the injection of argon gas will cause the tissue proximal to the tip 112 to reach a temperature between −160 and −170 degrees Celsius (° C.). This temperature will quickly cause an ice ball 220 of frozen tissue to form adjacent to the tip 112 and expand into the target tissue 200.

Figure 3:
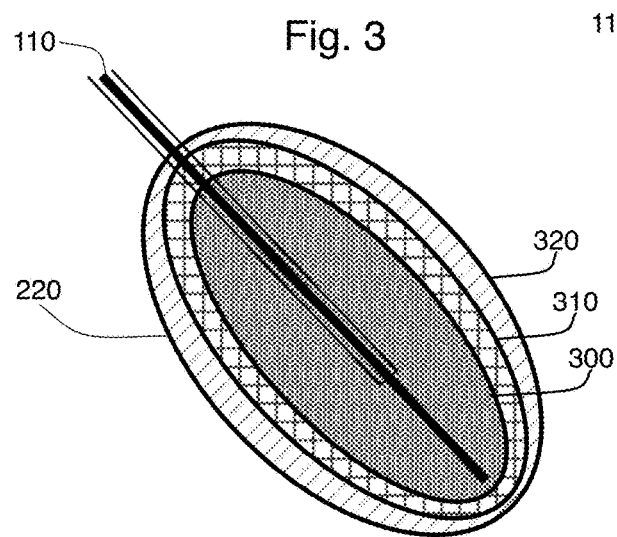
FIG. 3 is a schematic illustration of a generated ice ball with three isotherms illustrated.

While the temperature of the formed ice ball 220 near the probe may be below −160° C., the surface temperature of the ice ball 220 will remain at 0° C. To ensure destruction of the tissue, it is generally accepted that the tissue should reach a temperature of −40° C. or lower for approximately 3 minutes. This temperature will cause intracellular ice formation, which is destructive to most cells. Consequently, the abnormal tissue is typically frozen for three to five minutes during a cryoablation procedure. At this point, the ice ball 220 will have grown, as is shown in FIG. 3. After this time period, at least half of the diameter of the ice ball 220 will have reached −40° C. This is shown schematically in FIG. 3 by shaded area 300. The wider shaded region 310 shows the approximate location of the −20° C. isotherm, while the outer surface 320 of the ice ball 220 will have a temperature of −0° C.

Because only that portion of the ice ball 220 that has had a sustained temperature of −40° C. can be assured to have been destroyed, most cryoablation practitioners perform the procedure twice. After first forming the ice ball 220, the ice ball is allowed to thaw. The slow thawing of the frozen tissue in the ice ball 220 will cause further cell damage, as the thawing ice crystals will fuse to form larger crystals that cause further cell damage. The thawing process can be expediting by passing helium through the cryoprobe 110. Unlike cryogen gasses like argon, helium warms upon expansion. When helium passes through the cryoprobe 110, it will have the opposite effect of argon and will heat the tip 112 of the cryoprobe 110.

Figure 4:
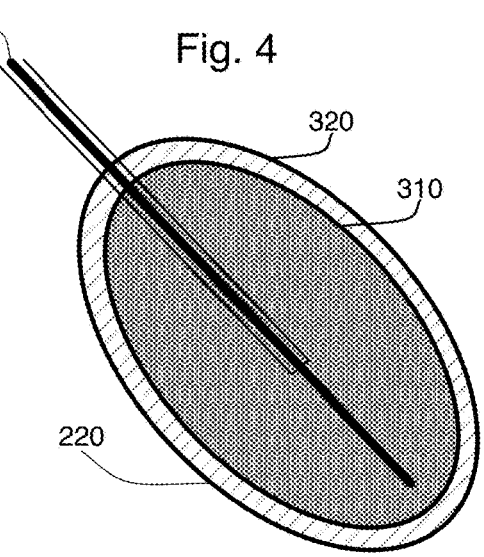
FIG. 4 is a schematic illustration of the generated ice ball of FIG. 3 after a second freeze.

The standard technique of freezing the abnormal tissue a second time after thawing will cause the freezing of the tissue to occur more rapidly (which is more destructive to the tissue). This allows complete tissue destruction at slightly warmer temperature, such as between −20° C. and −30° C. As a result, the effective treatment area of the procedure to move closer to the periphery 320 of the ice ball 220. As shown in FIG. 4, the shaded kill area will expand approximately to the −20° C. isotherm line 310. In most circumstances, the distance between the kill area and the periphery of the ice ball is believed to be between 4 and 10 mm. Because the outer areas of the ice ball 220 will be outside the assured treatment area 310, it is generally required to create an ice ball during cryosurgery that is larger than the tissue 200 desired to be destroyed.

Figure 5:
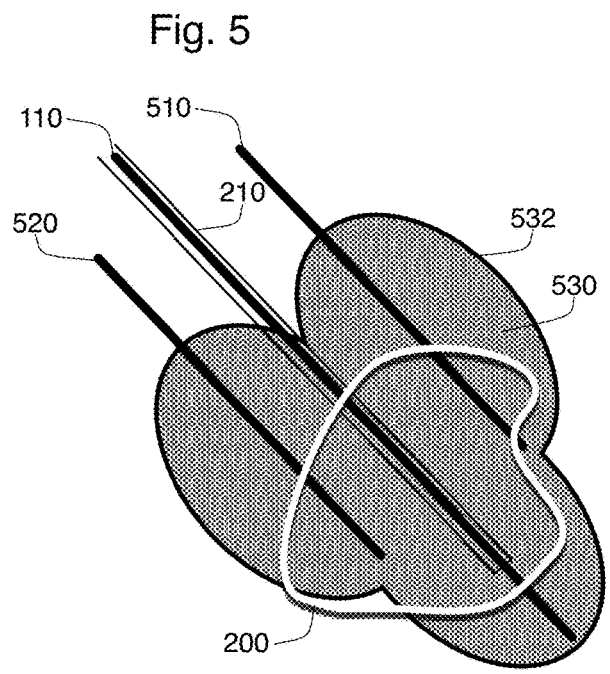
FIG. 5 is a schematic illustration of an irregular ice ball generated using three cryoprobes.

In some circumstances, it is necessary to create a different shape to the ice ball 220 in order to match the shape and size of the targeted tissue 200. In this circumstance, multiple cryoprobes can be inserted into different portions of the tissue 200. In FIG. 5, the first cryoprobe 110 is joined by a second cryoprobe 510 and a third cryoprobe 520. While these two additional cryoprobes 510, 520 may be inserted into the target tissue 200 using an introducer canula, it is only required that a single probe 110 use this sheath 210. When the three cryoprobes 110, 510, 520 are cooled, they work together to create a single ice ball 530 with a unified, but irregularly shaped surface 532. It is possible that some of the cryoprobes 110, 510, 520 will operate at different temperatures, with slightly warmer temperatures having a smaller freezing impact. Furthermore, the manufacturing of the cryoprobes 110, 510, 520 can influence the resulting shapes of the ice balls (with some probes creating a more spherical shape, for instance). By using differing designs and temperatures between the cryoprobes 110, 510, 520, it is possible to intentionally conform the resulting ice ball 530 into a shape that more effectively kills the target tissue 200 while minimizing damage to surrounding tissue. In FIG. 5, the resulting ice ball 530 did not destroy all of the target tissue 200, as some of the tissue 200 distal from the tip of cryoprobe 520 remains outside the boundaries of the formed ice ball 530. This is probably caused by the third cryoprobe 520 not being inserted far enough into the target tissue 200 before forming the ice ball 530.

Figure 6:
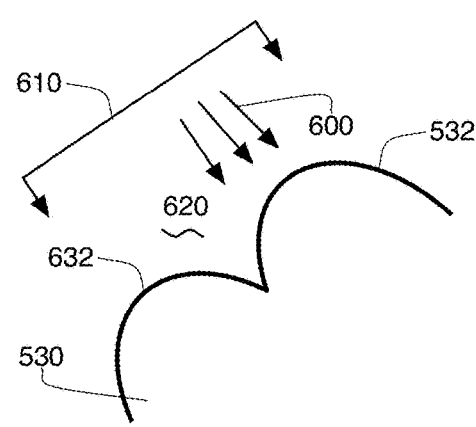
FIG. 6 is a schematic illustration of the irregular ice ball of FIG. 5 as seen by standard ultrasound technologies.

While the ultrasound device 100 that was used to guide the cryoprobes 110, 510, and 520 can be used to monitor the size and location of the ice ball once it has formed, this device 100 is limited in what it can see. As shown in FIG. 6, when the ultrasound device 100 is used to image the ice ball 530, the ultrasound acoustic energy 600 emanating from the device 100 will pass through unfrozen tissue 620 before hitting the ice ball 530. The device 100 is designed to monitor returning ultrasound energy. Using time and intensity information relating to this returning energy, an ultrasound imaging device can create a three-dimensional image of different tissues of the patient 120 encountered by the energy 600.

Unfortunately, the frozen nature of the ice ball 530 makes it extremely echogenic to ultrasound 600. In effect, the different physical characteristics between the thawed and frozen tissue, including the change in density of the tissue and the resulting change in the speed at which sound travels through the tissue, creates an acoustic impedance mismatch that causes the ultrasound energy to bounce off the ice ball. In addition, the ice ball itself will absorb ultrasound energy much more efficiently than unfrozen tissue. While the reflective nature of the ice ball 530 creates a clear image of the ice ball surface 532 using ultrasound, the ultrasound energy 600 cannot effectively penetrate beyond this surface 532. This creates an acoustic shadow behind this surface 532 which prevents any tissue or structure behind the surface 532 from appearing in the resulting ultrasound image.

In addition, because the ultrasound acoustic energy 600 emanates from a single device 100, the energy 600 essentially creates a plane of view 610 that defines that portion of the ice ball surface 532 that will be seen in the ultrasound images. This is true even if the device 100 utilizes a curved ultrasound array which sends out an arc pattern of ultrasound energy, or even if a phased array probe is used that sends out a pie-shaped pattern of energy. In each of these cases, the ultrasound energy 600 emanates from that single device that will define the effective plane of view 610. This means that the practitioner using the ultrasound device 100 will be able to see that the ice ball 530 formed at the correct proximal location, that the width of the ice ball 530 is wide enough to encompass the target tissue, and that the proximal surface 632 is sufficiently outside the target tissue 200 as to ensure destruction of the proximal portion of that tissue 200. However, since the practitioner cannot see into the shadow created beyond the closest surface 632 of the ice ball 530, she cannot determine whether the third cryoprobe 520 was inserted sufficiently deep within the target tissue 200.

Ultrasound Catheter

Figure 7:
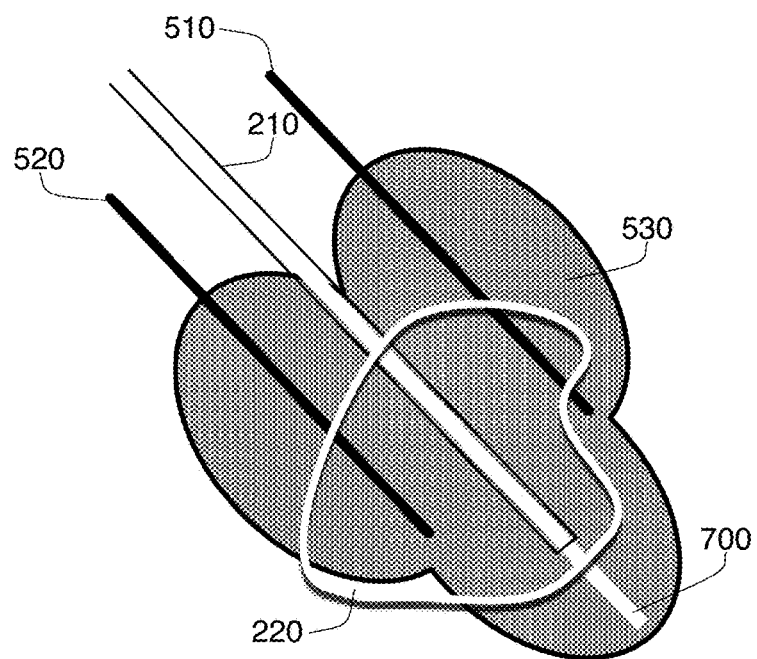
FIG. 7 is a schematic illustration of the irregular ice ball of FIG. 5 with one cryoprobe removed.

To overcome this issue, it is possible to withdraw cryoprobe 110 from the introducer canula 210 while the ice ball 530 is still frozen. Although the cryoprobe 110 may initially be frozen in place, a short application of helium will heat the cryoprobe 110 sufficiently to free the probe 110 without any significant thawing of the ice ball 530. FIG. 7 shows the ice ball 530 of FIG. 5 with cryoprobe 110 withdrawn. As shown in this figure, the removal of cryoprobe 110 leaves an opening or channel 700 within the ice ball 530.

Figure 8:
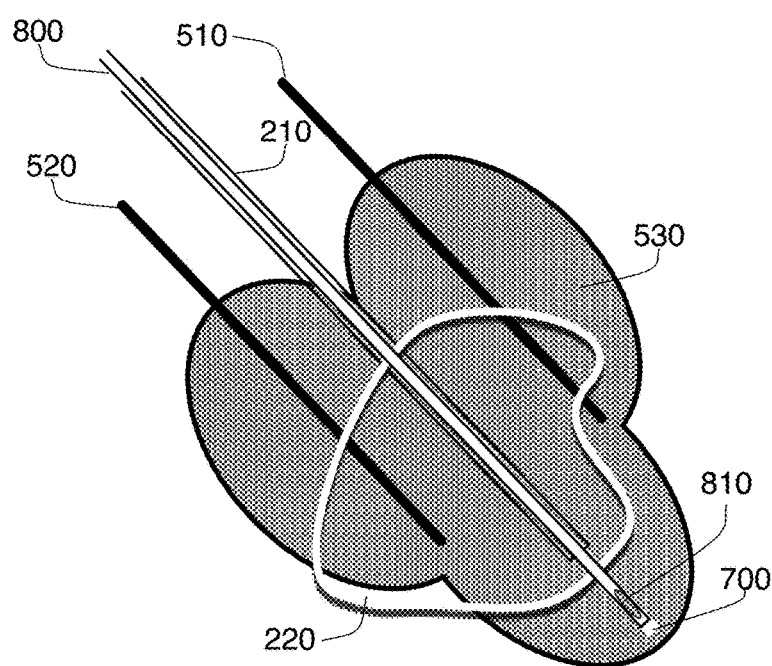
FIG. 8 is a schematic illustration of the irregular ice ball of FIG. 5 with an ultrasound probe inserted in place of the removed cryoprobe.

The fact that this channel 700 is in communication with the sheath 210 means that it is possible to insert an ultrasound catheter 800 into the ice ball 530, as shown in FIG. 8. This catheter 800 will include a plurality of ultrasound transducers 810 on its distal end. By inserting the ultrasound catheter 800 directly into the formed ice ball 530, a better understanding of the size and shape of the ice ball 530 can be generated.

The catheter 800 can be constructed according to the disclosures filed as U.S. Provisional Application Nos. 62/776,667 and 62/776,677, which were both filed by the owner of this application on Dec. 7, 2018. The entire contents of these two provisional applications are hereby incorporated by reference.

Figure 9:
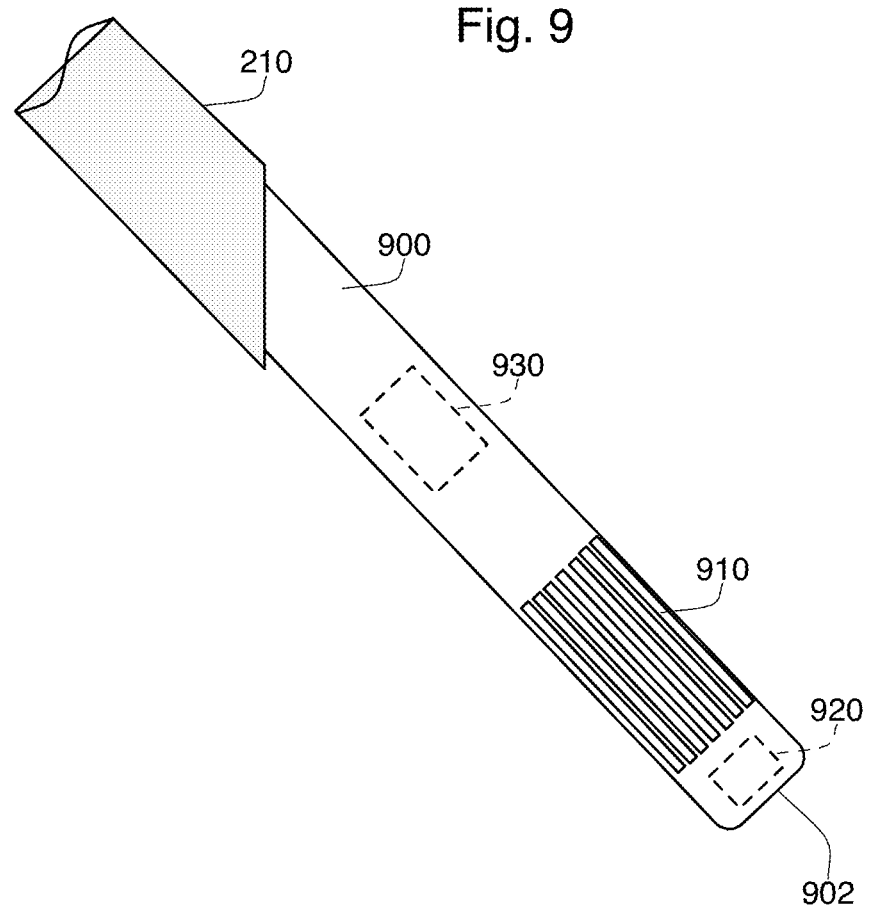
FIG. 9 is a plan view of the distal tip of one embodiment of an ultrasound probe within an introducer canula.

One embodiment of an ultrasound catheter 900 is shown in FIG. 9. This catheter 900 has a plurality of ultrasound transducer elements 910 near the distal end 902 of the catheter. In the preferred embodiment, a 64-element annular array of ultrasound transducers 910 are arranged around the periphery of the catheter 900. These transducers 910 may be PZT, pMUT, or cMUT based-transducers, and are able to transmit and detect varying frequencies of ultrasound energy, such as frequencies running from 4 to 50 MHz. Since FIG. 9 shows a plan view of the end of the ultrasound catheter 900, the individual transducers 910 appear to be co-planar, arranged on a flat surface of the catheter 900. While this is one potential configuration, in the configuration shown in FIG. 9, the transducers 910 are positioned around the periphery of a non-flat surface (such as an annular or cylindrical surface, such as that created by using a catheter having a circular, elliptical, or otherwise rounded cross-section).

The individual transducers 910 can form a phased-array, meaning that energy from multiple transducers 910 can work together to form a single directional beam of ultrasonic energy. This is generally performed by timing the transmission of ultrasound energy from a plurality of the transducers in order to create interference patterns in a single, controllable direction. The ultrasound energy transmitted in that direction will be larger than the amount of energy that could be transmitted from a single transducer. The same principal works while receiving energy, allowing the reception of energy at multiple transducers 910 to be separately and carefully delayed and analyzed so as to maximize the signal received by the transducers 910 from a single direction. Using this technique and the annular array of transducers 910 shown in FIG. 9, it is possible to transmit and receive ultrasound signals in a single radial direction from the transducers 910.

In other embodiments, a synthetic aperture technique is used. In this context, individual transmit pulses are sent and received unfocused. The beamforming algorithm then analyzes the previously unfocused signals after the fact in order to focus the transmission/reception of ultrasound energy in a single direction.

It is preferred to reduce the size of the ultrasound catheter 900 to as small a device as possible, preferably less than 2 mm in diameter, in order to allow the transducers 910 to enter the channel 700 created by removing the cryoprobe 110. In addition, although one embodiment is envisioned to have at least 64 imaging elements 910, other configurations from 16 to over 256 elements are possible. In fact, FIG. 16 (described below) shows an embodiment with only a single transducer element 1610.

In one embodiment, the ultrasound catheter 900 is capable of creating an image using traditional ultrasound imaging techniques. There are a variety of techniques for ultrasound imaging that could be applied, including gray-scale "B-mode" imaging to display echo amplitude in a scanned plane; M-mode imaging to track motion at a given fixed location over time; duplex, color, and power Doppler imaging to display motion in a scanned plane; harmonic imaging to display non-linear responses to incident ultrasound; elastographic imaging to display relative tissue stiffness; and contrast-agent imaging with contrast agents to display blood-filled spaces or with targeted agents to display specific agent-binding tissue types.

A less well-known ultrasonic imaging technology is based on quantitative ultrasound or (QUS), which analyzes the distribution of power as a function of frequency in the received echo signals backscattered from tissue. QUS exploits the resulting spectral parameters to characterize and distinguish among tissues. Use of QUS allows for the analysis of a very small sample of targeted tissue that effective creates an "acoustic biopsy" (AB) or (sonic biopsy) that can be performed on the tissue in situ. Furthermore, QUS can be used to analyze the tumor stroma and microvasculature nature to provide parameters related to cell death and/or apoptosis to provide confirmation or monitoring data of therapies such as chemotherapy, brachytherapy, cytotoxic agents (drugs) or ablation. This analysis can provide interim feedback of a tumor's response to therapy using parameters such as effective scatter diameter and effective acoustic concentration. The heterogeneity of a tumor or tissue stiffness can be analyzed by evaluating a nodule from multiple different directions and determining the depth of penetration of the ultrasound signal.

The preferred embodiment of the ultrasound catheter 900 further includes embedding electromagnetic (EM) sensors 920 at distal end 902. These sensors 920 can be used to navigate the catheter 900 within the patient 120. In practice, at least two sensors 920 are provided adjacent one another, but oriented differently within the catheter 900 in order to maximize the location and orientation information available. Veran Medical Technologies has developed a set of catheter systems that use EM sensors and EM navigation to accurately target and reach very small tissue masses. This technology is described in detail U.S. Pat. No. 8,696,549 entitled "Apparatus and Method for Four Dimension Soft Tissue Navigation in Endoscopic Applications," which is hereby incorporated by reference in its entirety. This document explains that, in most cases, a preoperative Computed Tomographic X-Ray (CT) scan can be used to build a model of an organ, such as the airways of the lungs, within a patient. Electromagnetic navigation during the procedure then uses sensors 920 on the catheter 900 to provide location and orientation information in 3D space. The EM 3D space is registered to the CT-created model, allowing the display of the location of the catheter on the organ model in real time. The Veran system also provides a fourth dimension of time varying tracking information. Respiratory tracking is performed that alters the apparent position of the probe in the virtual display to match the physical location of the EM sensors as they move with the body's respiratory motion, which is very useful in the present device.

In catheter 900, the EM sensors 920 and the array of ultrasound transducers 910 are both coupled to an electronics package 930. This electronics package is responsible for operating the individual transducers 910, and for transmitted received signals along a data transmission path (not shown) through the catheter 900 for digitized analysis and display to the practitioner. In one embodiment the electronics package 930 is responsible for multiplexing the signals from both the EM sensors 920 and the transducers 910 so that they can share a single data pathway along the catheter 900.

Ice Ball Size Determination

While the ultrasound catheter 900 is designed to be able to create standard ultrasound images (such as by using B-Mode imaging), and is designed to analyze particular tissue using QUS, such imaging techniques are not used to determine the size of the ice ball 530. Because of the nature of frozen tissue, the ultrasound energy transmitted through the tissue will travel much more quickly than through normal tissue. In addition, the absorptive nature of frozen tissue, and the risk of signal reflection before the ultrasound even enters the ice ball will make the creation of a normal ultrasound image almost impossible. Furthermore, the fact that all of the tissue at issue has been frozen may render it difficult to detect the normal tissue differences that can be seen in ultrasound.

Therefore, rather than generating an image of the ice ball 530, the catheter 900 will use a pulse-echo modality that effectively operates as sonar. The annular array of transducers 910 is first controlled to send an ultrasound signal in a single direction. Multiple transducers 910 may be utilized in sending this signal by create a beamformed signal. Alternatively, a single transducer 910 in the annular array can be used to send the ultrasound signal in that single direction. The amount of energy sent out in this signal pulse can be larger than the amount of sound energy that is normally transmitted during imaging. In effect, there is no need for subtlety in this pulse-echo technique—rather the energy transmitted should be maximized.

Figure 10:
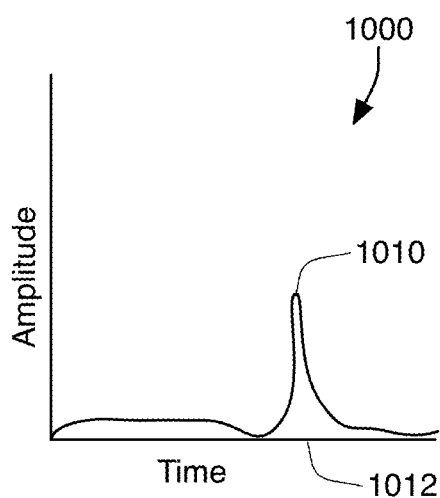
FIG. 10 is a first graph showing reflected ultrasound signal vs. time.

The same transducer or transducers 910 that transmit the pulse will also detect the ultrasound after it bounces back from the surface of the ice ball 530. As explained above, the impedance mismatch between the ice ball 530 and the surrounding unfrozen tissue 620 will cause a reflection of the ultrasound signal when it encounters the periphery 532 of the ice ball 530. This reflection will cause the signal to return to the transducers 910, where they will be detected after the time it takes for the sound energy to travel through the ice ball 530 to the surface 532 and then return. Using the phased-array techniques described above, multiple transducers 910 can receive this energy with the received energy being filtered to reveal only energy that was received from the same direction the energy was sent. Alternatively, the same single transducer that transmitted the signal in the single direction can receive the returned energy. The amplitude of the received sound energy can be graphed versus time, as seen in graph 1000 shown in FIG. 10. This graph 1000 shows that a large amount of ultrasound energy was received at peak 1010 of the graph 1000, which corresponds to time 1012. If time 1012 is T, and V is the speed of ultrasound through the frozen ice ball 530, the total distance traveled by the sound received at peak 1010 is D=V*T. Since the ultrasound must travel to the edge 532 of the ice ball 530 and back, the actual distance from the catheter 900 to the edge of the ice ball 530 in this direction is ½ V*T. Ultrasound generally travels through unfrozen tissue at approximately 1540 m/s. In frozen tissue, however, the speed of sound is significantly greater, and is between 2500 m/s and 4000 m/s. Furthermore, it is known that the speed of sound in frozen water increases as the temperature of the ice decreases, and it is expected that the same will be true of tissue frozen during a cryoablation treatment.

Figure 11:
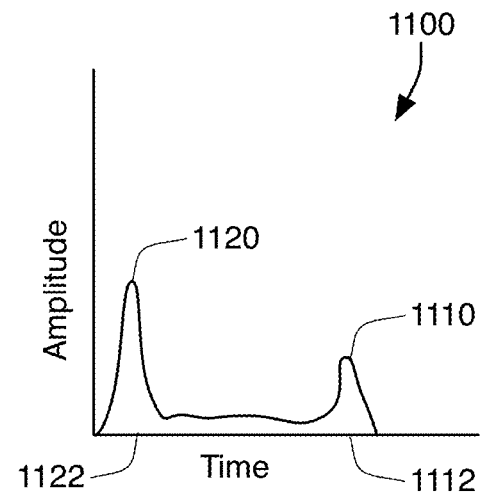
FIG. 11 is a second graph showing reflected ultrasound signal vs. time.

Graph 1000 shows a slightly idealized result of received ultrasound energy. In practice, it is likely that a significant portion of the ultrasound energy transmitted by the transducers 910 will be immediately reflected back at the initial boundary of the ice ball 530 within the channel 700. In this case, the received ultrasound energy may look closer to graph 1100 of FIG. 11. In this case, the outer boundary 532 of the ice ball 530 is seen at peak 1110 at time 1112. A significant peak 1120 at time 1122 is also seen, showing the immediate reflection from within the channel 700. This peak 1120 can be ignored when determining the size of the ice ball 530 and may not even be detectable if it occurs too quickly after the transmission of the pulse. It is preferred that the ultrasound transducers 910 be in contact with the frozen tissue of the ice ball 530 when inserted into the channel 700. This should reduce any initial reflection of ultrasound energy.

Figure 12:
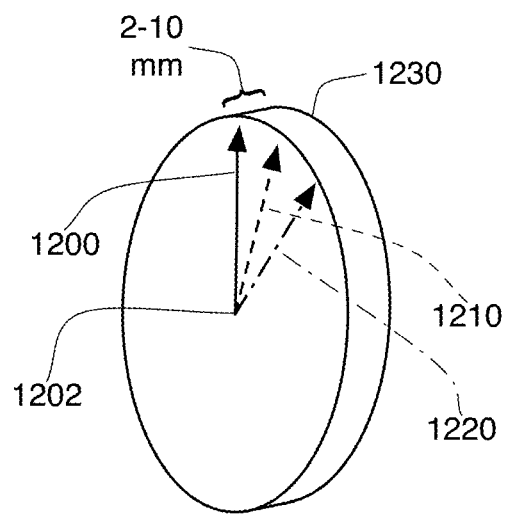
FIG. 12 is a schematic illustration of the computed dimensions of a single slice of an ice ball.

As explained above, the ultrasound pulse generated by the transducer(s) 910 will be transmitted in a single direction. This is seen as direction 1200 in the schematic diagram of FIG. 12. Using the time analysis of charts 1000/1100 and the above formula, the distance from the catheter 900 to the outer wall 532 of the ice ball 530 can be calculated. Once this has occurred, the transducers 910 will send another pulse is a different direction, such as direction 1210, and then determine the distance to the outer boundary 532 in that direction 1210. This is repeated in a third direction 1220 and then repeated throughout an entire 360-degree range of the transducers 910. At each direction, the distance to the outer boundary 532 is determined from the known location of the catheter 900 (location 1202 in FIG. 12). When these distances are combined as shown in FIG. 12, a slice 1230 indicating the size and shape of the ice ball perimeter 532 is created. In this embodiment, each pulse is transmitted radially away from the transducers 910 of the catheter 900 (location 1202), which means that the created slice 1230 will only represent the size of the ice ball 530 at the current position of the transducers 910.

Figure 13:
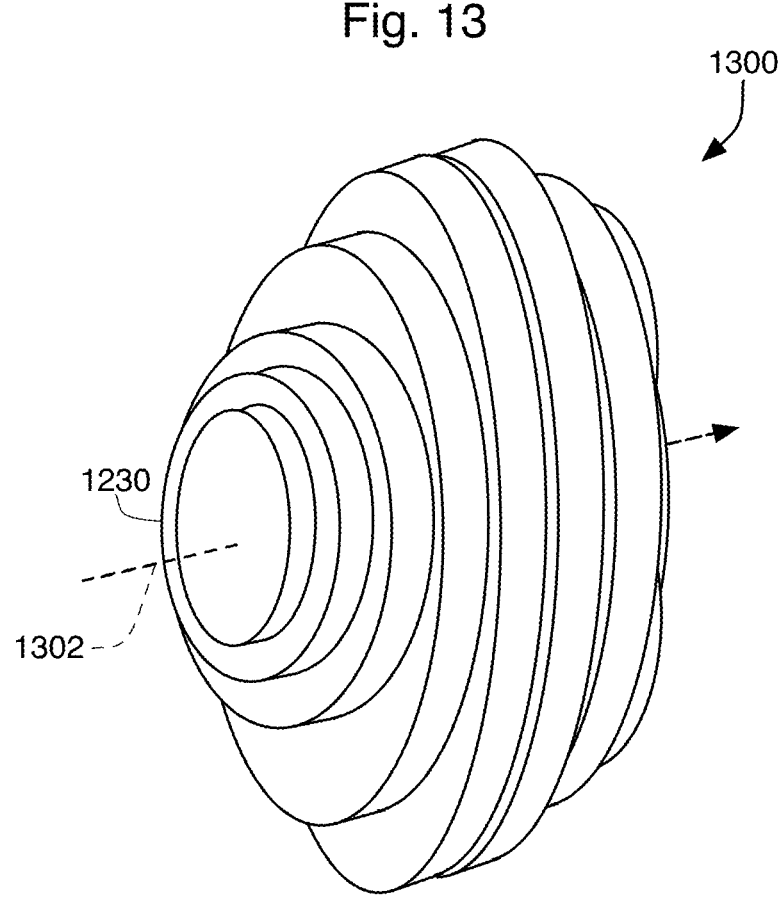
FIG. 13 is a schematic illustration of the computed dimensions of an ice ball consisting of a plurality of slices.

It is possible to repeat the process that created slice 1230 at different locations within the ice ball 530 by physically sliding the catheter 900 within the introducer canula 210. In one embodiment, the catheter 900 starts at the furthest location within the channel 700, and then is moved along the channel 700 between 2 and 10 mm between each created slice (such as slice 1230). When these slices are combined, a relatively complete model 1300 of the size and shape of the ice ball 530 is created, as shown in FIG. 13. To create these different slices, the catheter 900 is moved with respect to the channel 700 and introducer canula 210 along the path shown as element 1302 in FIG. 13. Note that this path 1302 is not an "axis" or "center point" for the slices that make up model 1300, as there is no requirement that the outer wall 532 of the ice ball 530 be centered around the channel 700 created by the cryoprobe 110.

As explained above, the physical location of the catheter tip 902 can be identified at all times using EM navigation and the signals created by EM sensors 920. As a result, the 3D model 1300 of the ice ball 530 can be positioned in 3D space, and then superimposed on registered CT images that show the target tissue 200. Using this technique, the practitioner can identify areas where the kill zone of the ice ball 530 has failed to encompass the target tissue 200. In some embodiments, the model of the target tissue 200 in the CT images is automatically compared to the 3D model 1300 of the ice ball 530, and the practitioner is automatically alerted to target tissue 200 that remains outside the effective zone of the ice ball 530. With this feedback, the practitioner can reinsert the cryoprobe 110 and refreeze the tissue using the existing locations of the probes 110, 510, 520 while using a longer or more intense freezing cycle. Alternatively, the practitioner can insert an additional probe to treat the unfrozen area of targeted tissue 200.

Process 1400

Figure 14:
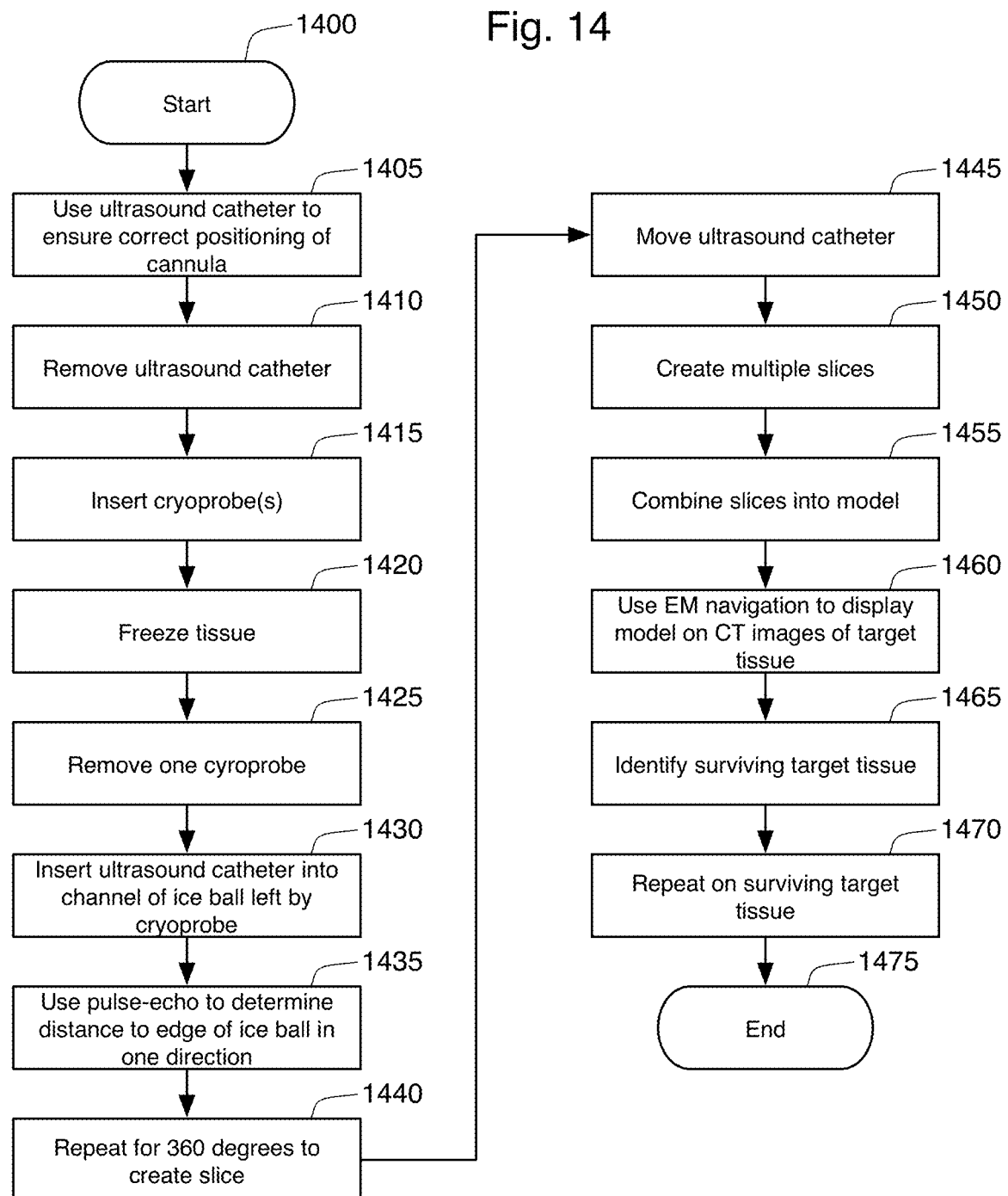
FIG. 14 is a flow chart showing a method for implementing one embodiment of the present invention.
Figure 15:
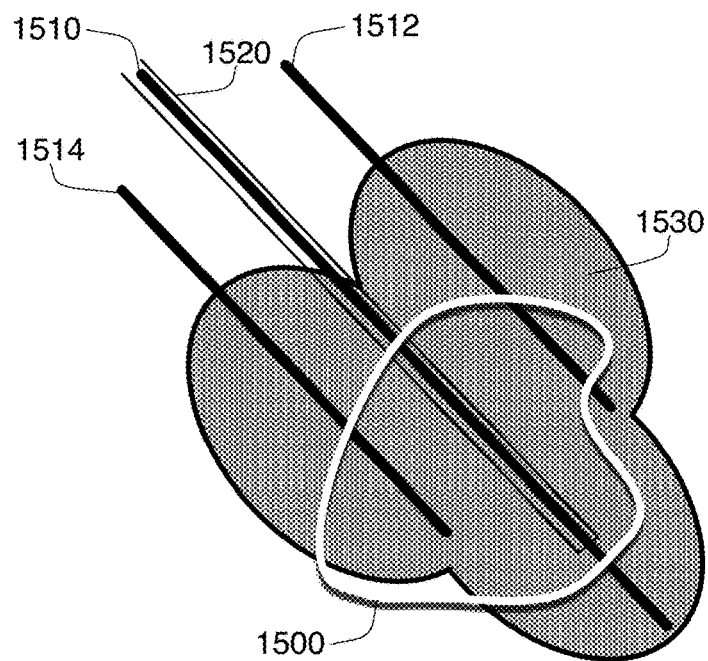
FIG. 15 is a schematic illustration of an irregularly shaped area of ablated tissue that was ablated using heat ablation.

The individual steps described above can be combined into process or method 1400, as shown in the flow chart of FIG. 14. The first step 1405 in this process is the only step that differs significantly from that described above. In connection with FIG. 1 and FIG. 2, it was explained that the ultrasound device 100 can help guide the cryoprobe 110 into the targeted tissue 200. In an alternative embodiment, the EM sensors 920 on the ultrasound catheter 900 can be directed to the targeted tissue 200 using EM navigation. Once the ultrasound transducers 910 are positioned within the (unfrozen) target tissue 200, an image of the tissue 200 can be obtained. In one embodiment, QUS is used to help diagnose or otherwise analyze the targeted tissue. The ultrasound imaging created by the sensors 910 at step 1405 can be used to ensure that the introducer canula 210 is appropriately placed for the insertion of the cryoprobe 110. At step 1410, the ultrasound catheter 900 is removed, and at step 1415 the cryoprobe 110 is inserted into the same location through the introducer canula 210. In some cases, additional cryoprobes 510, 520 may be inserted into the targeted tissue 200 in order to create an ice ball 530 of the appropriate size and shape.

At step 1420, the targeted tissue is frozen using the cryoprobe(s). As was also explained above, the freezing process frequently involves two different freezing operations separated by a thawing of the ice ball 530 in order to improve the effectiveness of the ice ball 530.

At step 1425, cryoprobe 110 is removed, creating a channel within the ice ball 530 that can be accessed through the introducer canula 210. At step 1430, the ultrasound catheter 900 is inserted into this channel.

The ultrasound catheter 900 is then used to create a 3D model of the size of the ice ball. This occurs through steps 1435 through 1455 of method 1400. At step 1435, a single direction is selected in which a pulse of ultrasound energy is transmitted. The echo from the outer edge 532 of the ice ball 530 in that direction is then detected. Using the known speed of ultrasound in frozen tissue, the distance from the catheter 900 to the outer edge 532 in that direction is determined. This is then repeated at different angles until the size and shape of a single slice of the ice ball 530 is determined at step 1440. The angle between each pulse is ideally determined using laboratory testing to obtain a good compromise between enhanced detail in the model of the single slice obtained by a small angle between pulses, and the speed of generating the model obtained by using a larger angle between pulses. As the speed of analyzing each pulse increases with improved computing technology, the preferred angle will decrease. In one embodiment, the angle between pulses is selected to be between 5 and 20 degrees. At step 1445, the catheter 900 is moved, and steps 1430 through 1445 are repeated in order to generate multiple slices, each showing the shape and size of the ice ball 530 at that location along the path of movement of the catheter 900 (step 1450). These multiple slices are then combined into a single 3D model of the ice ball 530 at step 1455.

Because the catheter 900 includes EM sensors 920, it is possible to locate, size, and orient the 3D model in the CT images used for EM navigation. Step 1460 displays the 3D model onto these images.

At step 1465, any portion of the targeted tissue 200 that appears to have been missed by the effectiveness of the created and modeled ice ball 530 are determined. This can be accomplished using computer software that compares the size, shape, and orientation of the 3D model against a known size, shape, and orientation of the targeted tissue 200. Since both the 3D model and the targeted tissue can be displayed simultaneously on the display, it is possible to present the surviving portions of the targeted tissue using some type of an identifiable distinguishing visual characteristic. For instance, the surviving tissue can be presented in a unique color or using a different brightness (brighter or darker) than the surrounding tissue. Whatever characteristic is used, it is important for the practitioner to be able to immediately see and identify what portion of the targeted tissue is not within the kill zone of the modeled ice ball 530. This surviving tissue can then be treated at step 1470. In some cases, the entire process 1405-1465 can be repeated by step 1470 to ensure that all of the targeted tissue 200 has been destroyed. In other cases, it will simply be necessary to refreeze one or more of the cryoprobes 110, 510, 520 in a manner that changes the size and shape of the ice ball 530 so as to effectively freeze the surviving targeted tissue. The method then ends at step 1475.

Heat Ablation Application

The new process for visualizing ablated tissue that was described above also has application outside of cryosurgery. Targeted tissue can be ablated through a variety of techniques, such as microwave ablation and radio-frequency ablation. Microwave ablation applies electromagnetic waves in the microwave spectrum (from 300 MHz to 300 GHz) to kill tissue in a targeted area. The water in the tissue absorbs the microwave radiation, thereby heating and killing the tissue. Radio-frequency ablation is similar, in that electromagnetic waves (this time in the radio-frequency spectrum) are used to heat and kill the targeted tissue. In both cases, the electromagnetic waves are transmitted by a needle that is inserted directly into the targeted tissue. The needle is guided to the targeted tissue in the same manner described above in connection with the cryoprobe 110 and then the heat producing signal is emitted from the end of the needle. The means that the need can be inserted percutaneously, laparoscopically, or during surgery. In each case, the needle can be inserted into the targeted tissue using an introducer canula such as canula 210 described above.

To apply the above-described techniques in the context of heat ablation, an RF or microwave ablation needle 1510 is inserted through the introducer canula 1520 and into targeted tissue 1500. In the context of microwave ablation, additional microwave needles 1512, 1514 can also be inserted into the target tissue 1500 in order to adapt the resulting shape of the ablation area 1530. It is not generally possible for multiple radio-frequency ablation needles to be active simultaneously. Nonetheless, it remains possible to have multiple ablation source locations in radio-frequency ablation by using multiple insertions of the same ablation needle, or by using different needles while insuring that no two needles are active at the same time. Regardless as to whether multiple needles or multiple insertions are used, the use of multiple ablation source location will create an irregularly shaped zone of ablated tissue 1530.

As explained above, physicians performing the ablation procedure need to know if the zone of killed/ablated tissue 1530 has successfully killed the targeted tissue 1500 with the patient. To determine this, the ablation needle 1510 inserted through the introducer canula 1510 is removed, and an ultrasound catheter is inserted through the same introducer canula 1510 into the middle of the ablated tissue 1530. Using the same techniques described above, it is possible to determine the size, shape, location, and orientation of the ablated tissue 1530 with respect to the targeted tissue 1500. Obviously, since the ablated tissue 1530 was heated instead of frozen, the calculations described above are slightly altered. It is known that ultrasound energy moves much faster through frozen tissue than normal tissue, and consequently it is difficult to image the frozen ice ball in three-dimensions using standard ultrasound imaging technologies. It is also true that ultrasound energy travels very differently through tissue ablated through heating 1530, and this difference once again makes it difficult to image the ablated tissue 1530 using standard ultrasound techniques. By using a pulse-echo technique and beamforming, and by modifying the above algorithms to use the speed of ultrasound energy in heat-ablated tissue as opposed to the speed within the ice ball, it is possible to generate a model of the ablated tissue 1530 and compare this model to the size and location of the targeted tissue 1500. As was described above in connection with cryotherapy, this process can determine that the heat-ablated tissue 1530 failed to include all of the targeted tissue 1500, resulting in the physician re-administering RF or microwave ablation to ensure that the portion of the targeted tissue 1500 outside the original heat-ablated area 1530 is properly treated.

Single Transducer Catheter

Figure 16:
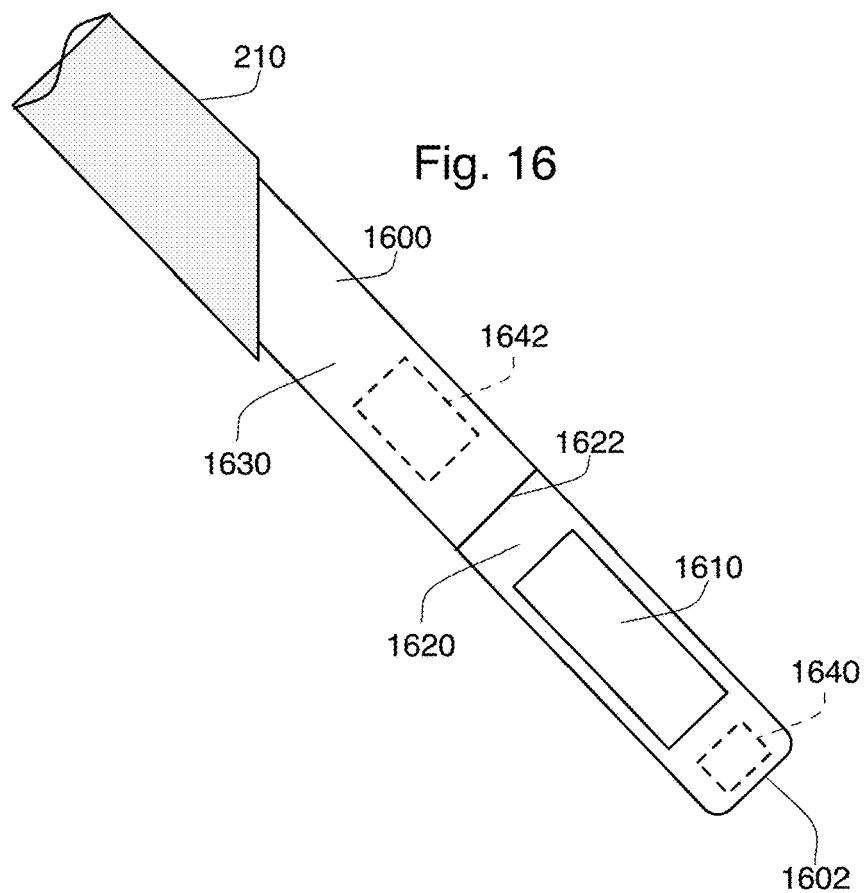
FIG. 16 is plan view of a distal tip of a second embodiment of an ultrasound probe within the introducer canula.

An alternative embodiment ultrasound catheter 1600 is shown in FIG. 16 with only a single transducer element 1610 proximal the tip 1602 of the catheter 1600. By using a single, larger transducer 1610, the amount of ultrasound energy transmitted perpendicular to the transducer 1610 could be maximized. The same large transducer 1610 would also be more sensitive in terms of receiving the reflected ultrasound energy from the distal boundary 532 of the ice ball 530. This single direction, single transducer pulse optimizes the ultrasound catheter 1600 for the sonar-like pulse required to perform the method 1400 described above.

The transducer 1610 is preferably flat, in one embodiment the transducer is located on a flat surface 1620 of the tip of the ultrasound catheter 1600. The flat surface 1620 may extend throughout the length of the catheter 1600, or it may terminate at position 1622 as should in FIG. 16. Position 1622 separates the tip portion having the flat surface 1620 from the remaining portion 1630 of the catheter 1600. The remaining portion 1630 can therefore have a circular or generally rounded cross-section for ease of movement within the introducer catheter 210. The cross-section of the tip portion having the flat surface 1620 may be semi-circular, with a rounded bottom portion (not shown) topped by the flat surface 1620 holding the transducer 1610.

As shown in FIG. 16, the catheter 1600 may also contain embedding electromagnetic (EM) sensors 1640 at distal end 1602. These EM sensors 1640 function as described above in connection with sensors 920. An electronics package 1642 is coupled to the single transducer 1610 and the EM sensors 1640 to control the signals sent to and received from these components.

The use of an ultrasound catheter having a single transducer 1610 allows for larger energy transmission in a single direction as well as better signal detection. Although the use of a single transducer 1610 greatly reduces the ability of the catheter 1600 to generate ultrasound images, this reduced functionality is irrelevant in the context of method 1400. However, the lack of the annular array of transducers 910 utilized on catheter 900 means that the single-transducer catheter 1600 must be rotated in order to generate the slices (such as slice 1230) described above. The rotation can be performed manually in the same manner that practitioners rotated other catheters. The requirement for a 360-degree rotation to be manually performed highlights the importance of the precise position measurements that are available only through the use of EM sensors 1640. Manual rotation of the catheter 1600 by a practitioner may result in inadvertent translational movement of the catheter 1600 with respect to the introducer catheter 210. Such inadvertent position changes can be registered by detecting the position of the EM sensors 1602. The exact current position of the catheter 1600 for each angular distance measurement (step 1435) may result in less than uniform "slices" but will result in an equally accurate overall model of the ice ball 530.

Figure 17:
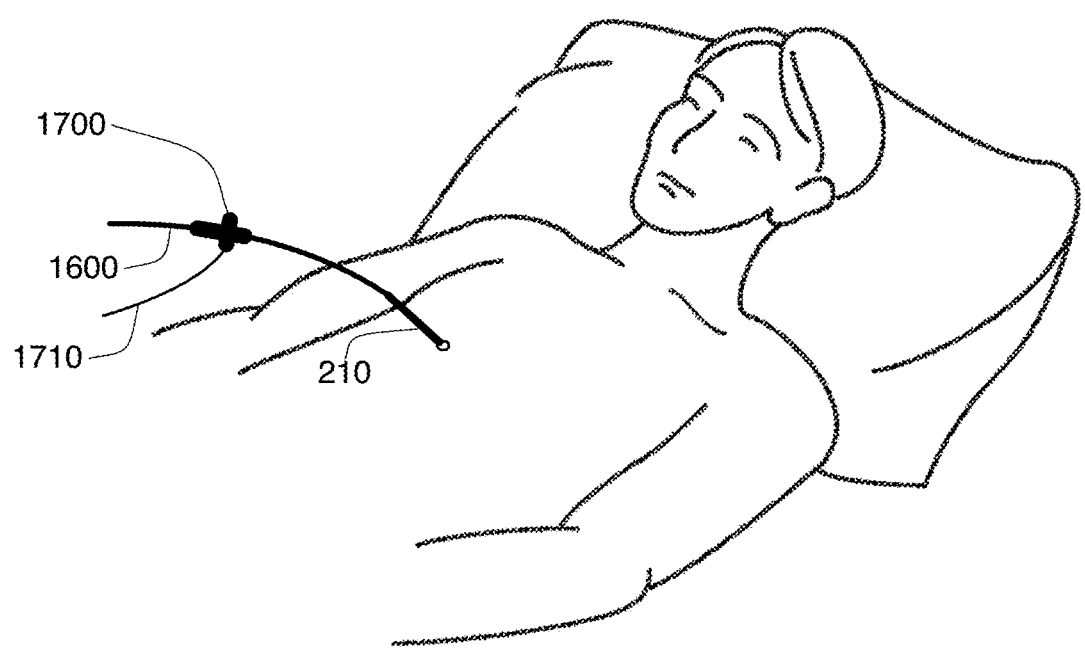
FIG. 17 is a side perspective view of the percutaneous insertion of an ultrasound probe that is rotated by an electric stepper motor.

An alternative embodiment is shown in FIG. 17, which shows the single-transducer catheter 1600 being used with a patient by inserting the catheter through introducer canula 210. Attached to the catheter 1600 is an electric stepper motor 1700. The stepper motor is physically engaged with the catheter 1600 so that the motor 1700 is able to control the rotation of the catheter 1600. The steps of the motor 1700 are associated with a given degree rotation of the catheter, so that control signals can be sent along control line 1710 to cause the motor 1700 to rotate the catheter 1600 as desired on command. In this way, the practitioner need not physically rotate the catheter 1600. Rather, the motor 1700, under the control of control line 1710, can time the rotation of the single transducer 1600 so that an entire slice measurement of the ice ball 530 can be performed as quickly and efficiently as possible with minimal translational movement of the transducer 1600 during the rotation cycle.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A method for cryoablation comprising:
   a) inserting a cryoprobe through an introducer canula into targeted tissue in a patient;
   b) generating an ice ball at a distal tip of the cryoprobe by cooling the distal tip of the cryoprobe;
   c) removing the cryoprobe from the introducer canula;
   d) inserting into the introducer canula an ultrasound catheter having an ultrasound transducer at a distal end;
   e) using the ultrasound transducer to transmit a directional ultrasound signal from within the ice ball and monitoring the ultrasound transducer for an ultrasound reflection from a surface of the ice ball;
   f) calculating a distance from the ultrasound catheter to the surface of the ice ball based on a time taken to receive the ultrasound reflection and a speed of ultrasound in frozen tissue;
   g) repeating steps e) and f) in different directions to generate information sufficient to model a slice of the ice ball;
   h) moving the ultrasound catheter within the introducer canula a known distance;
   i) repeating steps e) through h) to calculate and model a plurality of slices for at least a portion of the ice ball; and
   j) using a computer to combine the slices into an ice ball model showing a size and a shape for the portion of the ice ball.

2. The method of claim 1, further comprising:
   k) using the computer to determine an effective treatment area for the ice ball; and
   l) using the computer to compare the ice ball model against a known size and shape for the targeted tissue to identify portions of the targeted tissue outside the effective treatment area for the ice ball.

3. The method of claim 2, further comprising:
   m) repeating steps a) through j) on the portions of the targeted tissue outside the effective treatment area for the ice ball.

4. A method for treating a patient comprising:
   a) inserting an ablation catheter through an introducer canula into targeted tissue in the patient;
   b) ablating the targeted tissue using the ablation catheter to create an area of ablated tissue, wherein the area of ablated tissue has a known speed of ultrasound transmission that differs from a normal speed of ultrasound transmission in unablated tissue;
   c) removing the ablation catheter and inserting an ultrasound catheter into the introducer canula so that at least one ultrasound transducer on a distal end of the ultrasound catheter is positioned within the ablated tissue;
   d) transmitting, from the ultrasound catheter, a plurality of directional ultrasound pulses within the ablated tissue radially away from the ultrasound catheter, wherein the plurality of directional ultrasound pulses:
      i) are individually directed in a particular radial direction from the ultrasound catheter and are received from the particular radial direction,
      ii) are collectively transmitted in a plurality of radial directions, and
      iii) are collectively transmitted with the ultrasound catheter positioned in a plurality of different translational positions with respect to the introducer canula;
   e) determining, using a computer, a plurality of distances from the ultrasound catheter to an edge of the area of ablated tissue by using a time between the transmission and receiving of each pulse and by using the known speed of ultrasound transmission in the area of ablated tissue; and
   f) creating, using the computer, a model of the area of ablated tissue using the determined distance at the radial direction and the translational position for each pulse.

5. The method of claim 4, further comprising:
   g) displaying, using the computer, the model of the area of ablated tissue on a three-dimensional image of the patient showing the targeted tissue.

6. The method of claim 5, further comprising:
h) comparing on the computer the model of the area of ablated tissue against a known size and shape for the targeted tissue to identify portions of the targeted tissue outside an effective treatment area for the area of ablated tissue; and
i) displaying the identified portions of targeted tissue using an identifiable distinguishing visual characteristic.

7. The method of claim 5, wherein the distal end of the ultrasound transducer further contains electromagnetic sensors that receive electromagnetic signals that locate the distal end in an electromagnetic field, and further comprising using the received electromagnetic signals to display the model of the area of ablated tissue on the three-dimensional image of the patient.

8. The method of claim 4, wherein the ablation catheter is a cryoprobe and further wherein the area of ablated tissue comprises an ice ball.

9. The method of claim 4, wherein the ablation catheter is a heat ablation catheter and further wherein the area of ablated tissue comprises tissue killed through heat.

10. The method of claim 9, wherein the heat ablation catheter is a microwave ablation catheter.

11. The method of claim 9, wherein the heat ablation catheter is a radio-frequency ablation catheter.

12. The method of claim 4, wherein the ultrasound catheter has a plurality of ultrasound transducers at the distal end, further wherein a subset less than all of the ultrasound transducers are used to produce each of the ultrasound pulses, further wherein the subset is chosen based on the particular radial direction of each ultrasound pulse.

13. The method of claim 12, wherein the plurality of ultrasound transducers are arranged in an annular array around a circumference of the ultrasound catheter at the distal end of the ultrasound catheter.

14. The method of claim 13, wherein the subset of ultrasound transducers forms a phased-array transmitter that transmit each directional ultrasound pulse.

15. The method of claim 14, wherein the subset of ultrasound transducers that form the phased-array transmitter also form a phased-array receiver that receives each directional ultrasound pulse.

16. The method of claim 13, wherein the subset of ultrasound transducers forms a phased-array receiver that receives each directional ultrasound pulse.

17. The method of claim 4, wherein the ultrasound catheter has a single ultrasound transducer at the distal end, wherein the single ultrasound transducer transmits and receives the plurality of directional ultrasound pulses.

18. The method of claim 17, wherein the ultrasound catheter and the single ultrasound transducer are physically rotated to transmit the plurality of ultrasound pulses in the plurality of radial directions.

19. The method of claim 18, wherein a stepper electric motor physically rotates the ultrasound catheter.

20. A method for treating a patient comprising:
a) inserting an ultrasound catheter that is within an introducer canula into targeted tissue in the patient;
b) using the ultrasound catheter to perform QUS analysis on the targeted tissue;
c) replacing the ultrasound catheter with a cryoprobe without moving the introducer canula;
d) generating an ice ball by cooling the cryoprobe;
e) replacing the cryoprobe with the ultrasound catheter without moving the introducer canula; and
f) using the ultrasound catheter to determine a distance between the ultrasound catheter and a periphery of the ice ball by generating ultrasound energy within the ice ball.

* * * * *